United States Patent

Shorter et al.

[11] Patent Number: 6,083,265
[45] Date of Patent: Jul. 4, 2000

[54] FOOT AND SHIN COMPONENT FOR A LOWER LIMB PROSTHESIS

[75] Inventors: John Jeffrey Shorter, Nr. Chichester; Andrew John Sear Evans, Farnham, both of United Kingdom

[73] Assignee: Chas. A. Blatchford & Sons Limited, Basingstoke, United Kingdom

[21] Appl. No.: 09/038,410

[22] Filed: Mar. 11, 1998

[30] Foreign Application Priority Data

Nov. 21, 1997 [GB] United Kingdom .................... 9724680

[51] Int. Cl.⁷ ...................................................... A61F 02/74
[52] U.S. Cl. .............................................................. 623/27
[58] Field of Search ................................ 623/27, 28, 32, 623/47, 53, 55

[56] References Cited

U.S. PATENT DOCUMENTS

| | | |
|---|---|---|
| 2,684,487 | 7/1954 | Hansen et al. . |
| 3,400,408 | 9/1968 | Garcia . |
| 4,089,072 | 5/1978 | Glabiszewski ................................. 3/30 |
| 5,133,775 | 7/1992 | Chen . |
| 5,226,918 | 7/1993 | Silagy et al. ............................... 623/32 |
| 5,376,127 | 12/1994 | Swanson . |
| 5,425,780 | 6/1995 | Flatt et al. ................................. 623/38 |

FOREIGN PATENT DOCUMENTS

| | | |
|---|---|---|
| 0 454 524 A1 | 10/1991 | European Pat. Off. . |
| 41 25 635 A1 | 2/1993 | Germany . |
| 297 06 610 U1 | 7/1997 | Germany . |
| 2 084 025 | 4/1982 | United Kingdom . |
| 2 085 351 | 4/1982 | United Kingdom . |
| 2 304 289 | 3/1997 | United Kingdom . |
| 96/08216 | 3/1996 | WIPO . |
| 9706754 | 2/1997 | WIPO ...................................... 623/27 |

*Primary Examiner*—Michael J. Milano
*Assistant Examiner*—Alvin Stewart
*Attorney, Agent, or Firm*—Barnes & Thornburg

[57] ABSTRACT

A unitary foot and shin component for a lower limb prosthesis has a one piece thermoplastic endoskeletal foot keel and shin member and a continuous flexible cosmesis. The cosmesis includes a resilient foot body which is molded directly onto the keel so as to embed the keel, and an integral flexible and hollow shell which surrounds the shin member but is spaced from it. By forming the foot body and the hollow shell as a single polyurethane molding, the foot and shin can be supplied as a single component, ready for connection to a stump socket and alignment coupling.

25 Claims, 3 Drawing Sheets

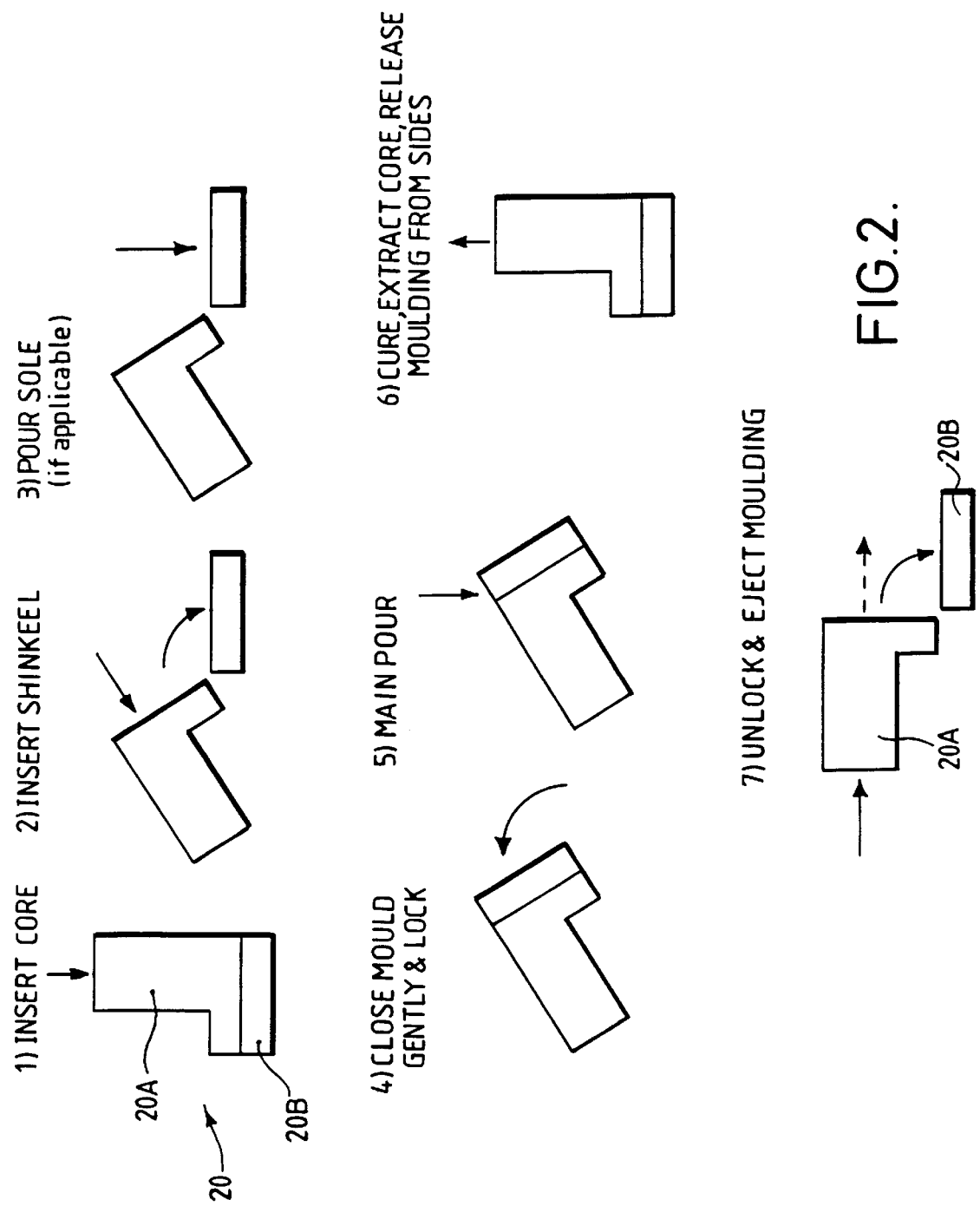

FOOT AND SHIN COMPONENT FOR A LOWER LIMB PROSTHESIS

FIELD OF THE INVENTION

This invention relates to a foot and shin component for a lower limb prosthesis, to a prosthesis containing the component, and to methods of making such a component and a lower limb prosthesis.

BACKGROUND OF THE INVENTION

It is known to manufacture an artificial foot by moulding a resilient elastomeric foot body around an endoskeletal keel member, with the keel member projecting from a proximal face of the moulding to provide an interface for connecting the foot to an endoskeletal shin member. Typically, in a below-knee lower limb prosthesis, the shin member carries, at is proximal end, an alignment coupling and, above the alignment coupling, a stump socket for receiving the amputee's stump. To cover the shin member, it is common to slide a foam sleeve over the shin member, the inner surface of the sleeve closely fitting the shin member and the outer surface being shaped to correspond approximately to the shape of a human shin. The distal end of the sleeve abuts the proximal surface of the foot body.

It is an object of this invention to allow a lower limb prosthesis to be manufactured more simply, especially in locations where sophisticated equipment and skilled personnel are unavailable.

SUMMARY OF THE INVENTION

According to a first aspect of this invention, there is provided a unitary foot and shin component for attachment to a proximal limb component of a lower limb prosthesis, wherein the unitary component comprises endoskeletal foot keel and shin members and a flexible moulded cosmesis, the cosmesis comprising a resilient foot body and, integral with the foot body, a moulded flexible and hollow shell surrounding at least the major part of the shin member, the keel member being embedded in the foot body so as to be integral therewith. The shell may define an interior cavity which extends distally to a location at or adjacent the distal end of the shin member where in the preferred embodiment, it merges into the foot member.

This component can be manufactured, and supplied to the location where the prosthesis is to be fitted to the amputee, as a single component. Preferably, the only other components required at the fitting location, at least in the case of a below-knee prosthesis, are an appropriate stump socket and a connector, typically in the form of an alignment coupling with a clamp for the shin member, for connecting the shin member to the socket. If the proximal end portion of the shin member of the supplied component is of constant cross-section, the member may be cut to a selected length prior to connection of the component to the socket. Typically, in this case, the keel member and the shin member are an integral one-piece component.

The flexible hollow shell may be made of the same material as at least an outer skin of the foot body and integrally formed with the skin, or the foot body and the shell are all integrally formed as a single moulding of foam material, preferably polyurethane foam material. By making the hollow shell extend beyond the proximal end of the shin member and arranging for the thickness of the shell, at least in a region adjacent its proximal end, to be in the range of from 1.5 mm to 4 mm, assembly of the prosthesis may consist simply of the steps of rolling the shell down to expose the proximal end of the shin member, cutting the shin member to length, and coupling the shin member to the socket, typically using the above-mentioned connector including an alignment coupling, and then unrolling the shell proximally to fit around at least the distal portion of the socket. If required, the space between the shell and the shin member may be filled with a lightweight material such as loose polystyrene beads or an alternative lightweight material prior to unrolling the shell to cover the alignment coupling.

In the preferred foot and shin component in accordance with the invention, the foot body comprises a moulding which embeds the keel member by being moulded directly onto the keel member. The preferred foam material, particularly in the case of the foot body and the shell being integrally formed as a single moulding, is a skin-coloured polyester polyurethane. Such a material is sufficiently flexible to allow manipulation of the hollow shell as described above, in which case the shell thickness is typically 2 mm to 3 mm. It has good wear properties which allow the foot body to be used without shoes, and, being self-foaming, it forms a skinless foam which can also penetrate thin mould sections, thereby to form the hollow shell to the required thickness. The material is sufficiently resilient that the foot body provides a cushioned heel, dispensing with the need for an ankle joint.

Where a skin is required, a polyether polyurethane material is preferred.

It will be appreciated from the above, that the component can be used to form a below-knee lower limb prosthesis including a stump socket for receiving the amputee's stump, and means for connecting the stump socket to the foot and shin component, wherein the hollow shell is of sufficient length to surround the connecting means and at least a distal portion of the socket. However, the invention is not limited to a below-knee prosthesis. With a suitable termination of the cosmesis at the proximal end, the shin member can be coupled to a knee mechanism of an above-knee prosthesis.

The invention also provides a method of making a unitary foot and shin component as described above, the method comprising providing an endoskeletal foot keel and shin structure, placing the endoskeletal structure in a mould which encloses the keel part of the structure and at least the major part of the shin part of the structure, introducing a liquid plastics material into the mould to surround the keel part, and allowing the material to set to form a resilient mass in which the keel part is embedded. Where the component is to be produced as a single-piece moulding, using a single moulding material, the mould is a rigid container which provides a mould surface shaped to correspond generally to the shape of the human foot and shin, and has a rigid mould core having an outer surface shaped to correspond generally to that part of the container having a mould surface generally in the shape of the human shin, such that with the core fitted inside the container they define together a mould cavity of thin annular cross section. The endoskeletal structure is inserted into the container with the shin part of the structure within a longitudinal passage in the core, and liquid plastics material is then introduced into the mould so as (a) to surround the keel part to form a resilient body embedding the keel part and shaped in the shape of a human foot, and (b) to enter the annular mould cavity to form a flexible hollow shell which is integral with the foot body and is in the shape of a human shin.

In an alternative preferred method, the mould is, itself, a flexible hollow plastics envelope which is shaped to correspond generally to the shape of the human foot and shin and which becomes the outer layer of the cosmesis. Thus, when the endoskeletal structure is held inside the envelope, liquid plastics material is introduced into the envelope to surround the keel part but without covering the shin part whereby, when the material sets, it forms, together with the plastics envelope, an integral cosmesis comprising (a) a resilient body containing the keel part, which body includes a flexible outer skin and is in the shape of a human foot, and (b) a hollow shell which is integral with the foot body and is in the shape of a human shin.

The invention will be described in more detail below by way of example and with reference to the drawings.

BRIEF DESCRIPTION OF THE DRAWINGS

FIG. 2 is a process diagram showing a preferred moulding method.

DETAILED DESCRIPTION OF THE PREFERRED EMBODIMENTS

Figure 1:
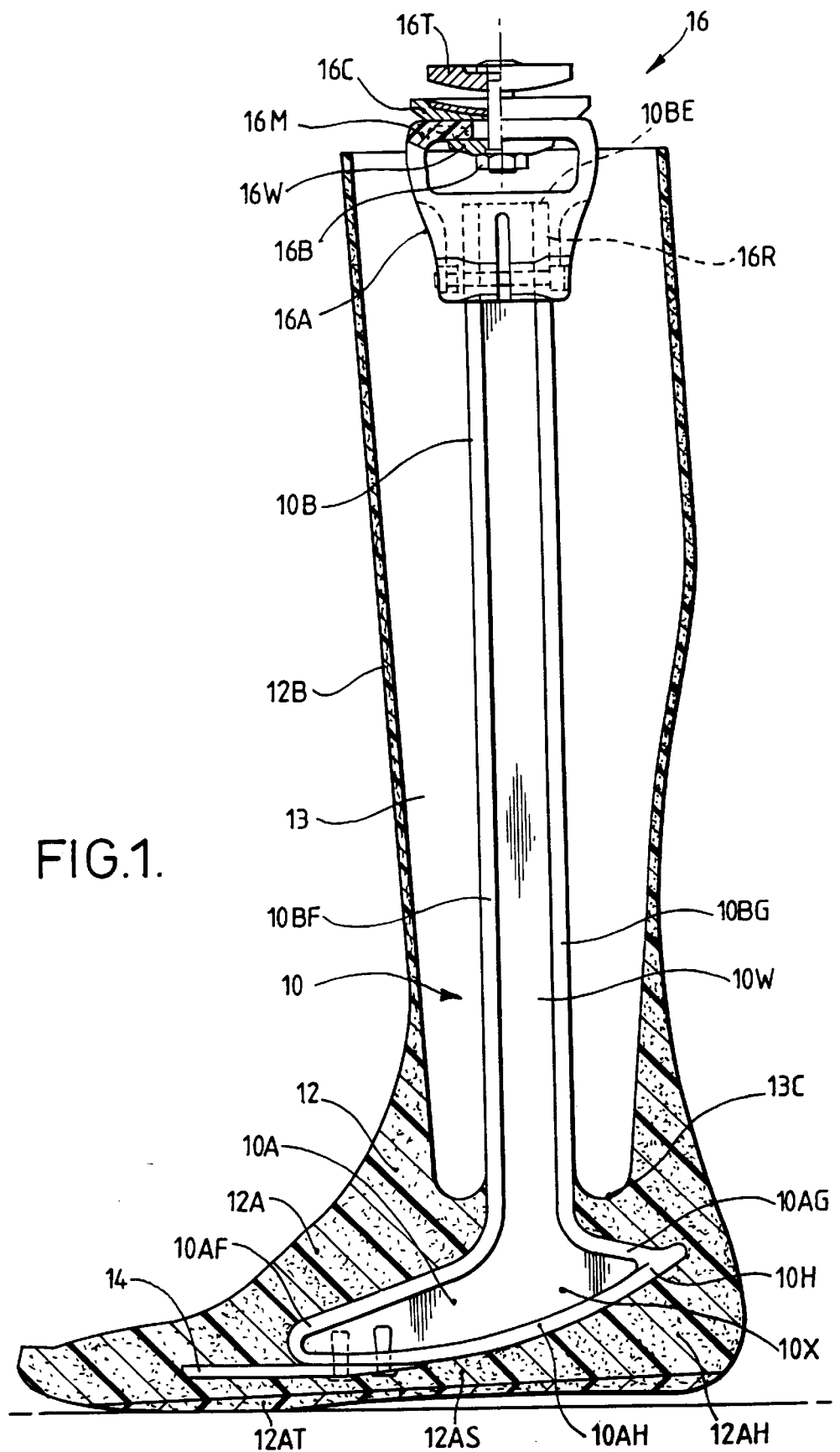
FIG. 1 is a partially sectioned side view of a foot and ankle component in accordance with the invention, together with a proximal connecting component.

Referring to FIG. 1, a unitary foot and shin component for attachment to a proximal limb component of a below-knee lower limb prosthesis has a one-piece injection-moulded fibre-reinforced thermoplastics endoskeletal structure 10 having a foot keel member 10A and a shin member 10B. The two members 10A, 10B form a substantially rigid unit. Surrounding the endoskeletal structure is a flexible elastomeric cosmesis 12 comprising a resilient foam foot body 12A in the shape of the human foot and, integrally formed with the foot body 12A, a hollow flexible shell 12B surrounding and spaced from the shin member 10B, and extending beyond the proximal end 10BE of the latter. The shell 12B defines an annular interior cavity 13 which is proximally open and distally closed, the closed end 13C being formed by the foot body immediately above the keel member 10A.

The one-piece endoskeletal structure 10 is described in detail in British Published Patent Application No. (2304289A), the disclosure which is incorporated in the present specification by way of reference. The shin member 10B has an H-shaped cross section with the web 10W of the H lying in an anterior-posterior plane. The keel member 10A has a coplanar web 10X, bounded at its upper edges by flanges 10AF and 10AG which merge directly into the flanges 10BF and 10BG of the H-section shin member 10B, respectively, while the lower edge is bounded by a lower flange 10AH forming a sole plate which is convexly curved so as to have a proximally inclined heel portion 10H.

Attached to the anterior end portion of the keel member is an anteriorly-extending resilient blade 14.

When the unitary foot and shin component is incorporated in a below-knee lower limb prosthesis, the shin member 10B carries a connector 16 for connecting the components to a stump socket (not shown). Connector 16 takes the form of an injection-moulded fibre-reinforced thermoplastics clamp member 16A having an H-section clamping recess 16R, and a mounting plate 16M. The mounting plate supports an alignment cup member 16C for receiving the convex end portion of the stump socket, the socket wall being trapped between the cup member 16C and a trapping plate 16T which is tightened onto the inner face of the socket by a bolt 16B threaded in the trapping plate and passing through a washer 16W and an oversized hole in the mounted plate 16M.

In the preferred embodiment, the cosmesis 12 is a single moulding in the sense that both the foot body 12A and the hollow shell 12B are moulded in one operation using the same foam material for both parts 12A, 12B. The preferred material is a polyester polyurethane foam material. In the foot body 12A, the material forms a solid foam mass surrounding the keel member 10A on all sides. A sole portion 12AS is formed beneath the sole plate 10AH which, in the region of the heel, is of increased thickness due to the upwardly inclined orientation of the plate 10AH in that region, thereby forming a resilient heel cushion 12AH.

Over substantially the whole length of the shin member 10B, the cosmesis 12 is hollow and of annular cross-section, being shaped generally in the shape of the human shin. The polyurethane material is skin-coloured so that the cosmesis may be used without any further covering.

Figure 1A:
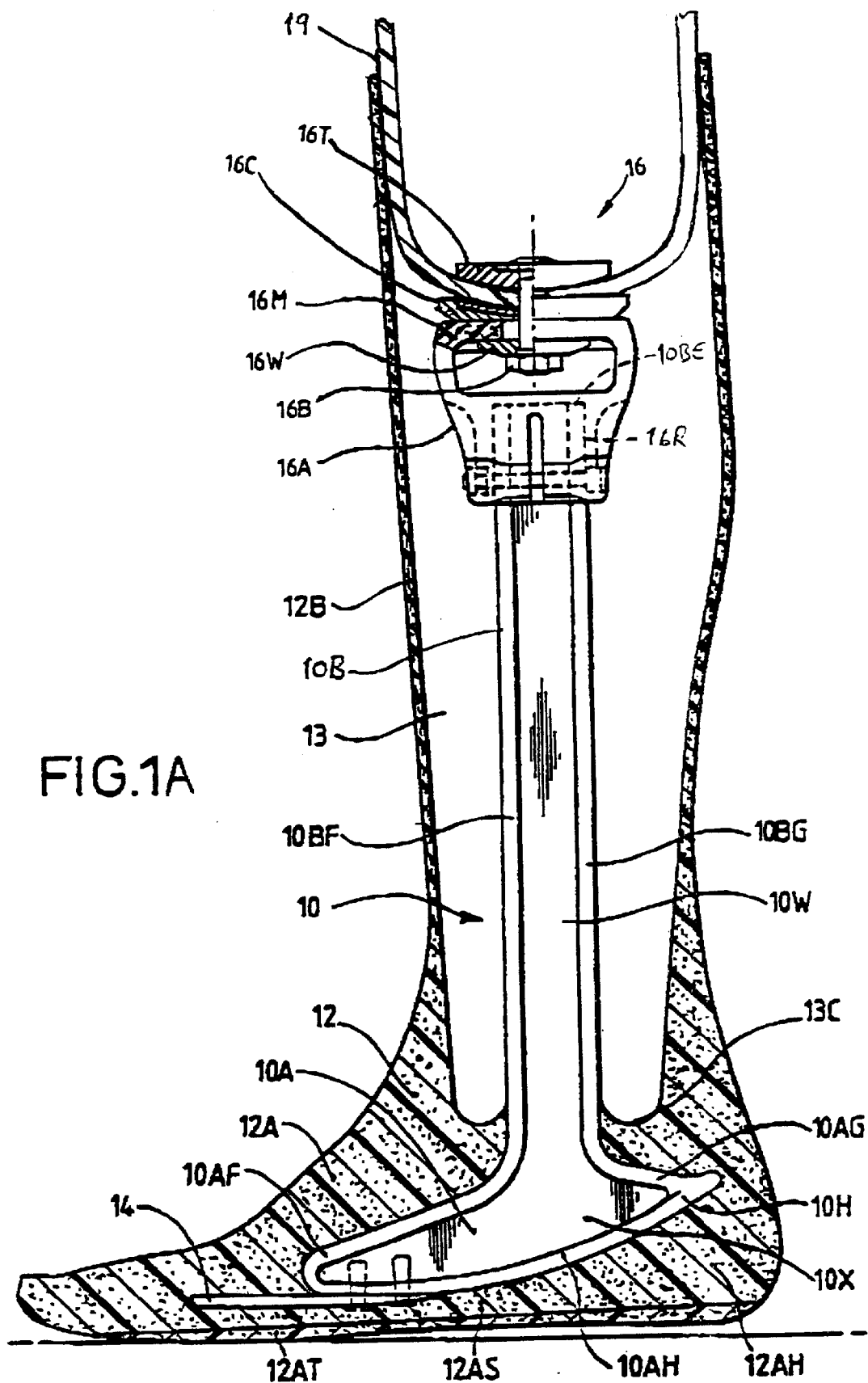
FIG. 1A is a partially sectioned side view of the foot and ankle component shown in FIG. 1 which further shows a hollow shell portion of the foot and ankle component arranged at its proximal end to be fitted over and grip a distal portion of a stump socket of the connecting component.

Although in FIG. 1 the hollow shell is shown as extending to the level of the alignment coupling, it may extend further in the proximal direction so as to be coextensive with a distal portion of the stump socket 19, as shown in FIG. 1A; in which case the diameter of the hollow shell adjacent its proximal end is arranged to be such that, when stretched, it may be fitted over and grip the distal portion of the socket 19. In the case of a polyester polyurethane, the thickness of the hollow shell, at least in the distal end portion, is in the region of 2 mm to 3 mm so that it may be rolled down to expose the proximal end of the shin member during assembly of the prosthesis. The thickness of the shell may be outside this range, depending on the characteristics of the particular material selected, and depending on the required interface between the proximal end of the shell and other components of the prosthesis.

Other materials may be used, e.g. a polyether polyurethane, depending on the selected method of moulding and the required characteristics of the cosmesis. This material forms a thin skin when moulded and, typically, the thickness of the hollow shell, at least in the distal end portion, is 2 mm to 2.5 mm.

Although the preferred embodiment described here uses a single polyurethane material for the whole of the cosmesis 12, in some circumstances, depending on the characteristics required, a different (e.g. harder-wearing) material may be selected for the sole of the cosmesis, according to wear requirements. This feature appears in FIG. 1 as a lower sole layer 12AT.

One preferred method of moulding the cosmesis is shown diagrammatically in FIG. 2. The mould takes the form of an outer container 20 which is in two parts: a first part 20A for forming the upper part of the foot body and the hollow shell, and a lower part 20B for forming the lower half of the foot body. These two parts together form a container having inner moulding surfaces shaped so as to correspond generally to the shape of the human foot and shin. The mould also includes a core (not shown) with an outer moulding surface shaped to correspond generally to the inner moulding surface of the container which forms the hollow shell (the shin). The core has a longitudinal H-section passage for receiving the shin member of the endoskeletal structure 10 (see FIG. 1).

The moulding method comprises the following steps:

1) Insertion of the core in the upper container part 20A of the mould, insertion being from the proximal end ("proximal" here referring to the proximal direction of the moulded cosmesis when incorporated in a lower limb prosthesis).
2) Insertion of the endoskeletal structure into the longitudinal passage of the core, insertion occurring from the distal end of the core with the two parts of the container separated.
3) Formation of the sole wear layer (if applicable) by pouring a polyurethane mixture into the lower part 20B of the container so as to form a hard-wearing sole pad.
4) Closure of the mould container by bringing together container parts 20A and 20B while the sole pad is still tacky.
5) Pouring a mixed polyurethane liquid foam material through an opening in the heel region and with the mould oriented such that the heel region of the mould cavity is higher than other parts of the cavity and such that the material flows as a foam into both the cavity forming the foot body and the annular cavity forming the hollow shell of the cosmesis.
6) Curing of the poured polyurethane material, extraction of the core proximally from the upper part 20A of the mould container, and release of the moulding from the sides of the mould container.
7) Separation of the container parts 20A, 20B and ejection of the moulding distally from the upper container part 20A.

In an alternative method of manufacture, the first step is the manufacture of a hollow cosmesis skin or layer using, for instance, a polyester polyurethane material and a blow-moulding process so that the outer surface of the skin corresponds generally in shape to the shape of a human foot and shin. This blow moulded component is hollow both in the shin and the foot. Next, the endoskeletal structure is suspended inside the hollow component in a required position with the shin member substantially vertical and the foot keel member at the bottom, spaced from the sole part of the blow-moulded skin. Liquid plastics material (again, a polyurethane foam material may be used) is poured into the hollow component to fill the foot region and to embed the foot keel member, while leaving the major part of the shin member uncovered. When this poured material sets, at adheres to the inside of the previously formed shin, as well as to the foot keel member, to form a unitary foot and shin component with an integral cosmesis, in accordance with the invention.

While the invention has been shown and described with reference to preferred embodiments, it will be understood by those skilled in the art that changes in form and detail may be made without departing from the spirit of the invention, the scope of which is as set forth in the claims.

What is claimed is:

1. A unitary foot and shin component for attachment to a proximal limb component of a lower limb prosthesis, wherein the unitary component comprises endoskeletal foot keel and shin members and a flexible moulded cosmesis, the cosmesis comprising a resilient foot body and, integral with the foot body, a moulded flexible and hollow shell surrounding at least the major part of the shin member, the keel member being embedded in the foot body so as to be integral therewith.

2. A component according to claim 1, wherein the hollow shell is made of the same material as and is integrally formed with at least an outer skin of the foot body.

3. A component according to claim 1, wherein the foot body and the shell are integrally formed as a single moulding of foam material.

4. A component according to claim 3, wherein the foam material is polyurethane.

5. A component according to claim 2, wherein the foot body comprises a flexible outer skin and an inner foam mass, the foam mass embedding the keel member and filling the outer skin of the foot body.

6. A component according to claim 1, wherein the foot body comprises a moulding moulded directly onto the keel member so as to embed the keel member.

7. A component according to claim 1, wherein the thickness of the shell, at least in a region adjacent its proximal end, is in the range of from 1.5 mm to 4 mm, and the shell defines an annular interior cavity which extends over substantially the whole of the length of the shin member to a location adjacent the foot member.

8. A component according to claim 1, wherein the thickness of the shell, at least in a region adjacent its proximal end is in the range of from 2 mm to 2.5 mm.

9. A component according to claim 1, wherein the cosmesis is a single piece foam moulding, moulded from polyester polyurethane.

10. A component according to claim 1, wherein the cosmesis is a single piece foam moulding, moulded from polyether polyurethane.

11. A component according to claim 1, for a below-knee prosthesis, wherein the cosmesis extends beyond the proximal end of the shin member.

12. A component according to claim 1, wherein at least the proximal end portion of the shin member is of constant cross section to allow the member to be cut to a selected length prior to attachment of the component to the proximal limb component, and wherein the keel member is integral with the shin member.

13. A lower limb prosthesis including a unitary foot and shin component as claimed in claim 1.

14. A below-knee lower limb prosthesis including a unitary foot and shin component as claimed in claim 1, a stump socket for receiving the amputee's stump, and means for connecting the stump socket to the foot and shin component, wherein the hollow shell is of sufficient length to surround the connecting means and at least a distal portion of the socket.

15. A prosthesis according to claim 14, wherein the diameter of the proximal end of the shell is such that it is stretched around the socket distal portion.

16. A component according to claim 1, wherein the foot body comprises a single-piece solid foam mass surrounding the keel member.

17. A method of making a unitary foot and shin component as claimed in claim 1, the method comprising providing an endoskeletal foot keel and shin structure, placing the endoskeletal structure in a mould which encloses the keel part of the structure and at least the major part of the shin part, introducing a liquid plastics material into the mould to surround the keel part, and allowing the material to set to form a resilient mass in which the keel part is embedded.

18. A method according to claim 17, wherein the mould is a rigid container which provides a mould surface shaped to correspond generally to the shape of the human foot and shin, and a mould core having an outer surface shaped to correspond generally to that part of the container having a mould surface generally in the shape of the human shin such that with the core fitted inside the container they define together a cavity of thin annular cross section, wherein the method further comprises inserting the endoskeletal structure into the container with the shin part of the structure within a longitudinal passage in the core, and wherein the liquid plastics material is introduced into the mould so as (a) to surround the keel part to form a resilient body embedding the keel part and shaped in the shape of a human foot, and (b) to enter the said annular cavity to form a flexible hollow shell which is integral with the foot body and is in the shape of a human shin.

19. A method according to claim 18, wherein the mould container has a shin and upper foot part and a sole part which is detachable from the shin and upper foot part, and wherein the core is removably fitted in the shin and upper foot part of the container, the method comprising:

inserting the core in the shin and upper foot part of the container, inserting the endoskeletal structure into the core, securing the container parts together, introducing the liquid plastics material into the container, and when the material has set to form a moulding, removing the core from the container, and removing the moulding from the container.

20. A method according to claim 19, wherein the liquid is introduced into the mould container with the container oriented such that the part of the interior space of the container which corresponds to the heel of the resulting moulding is higher than the other parts of the interior space.

21. A method according to claim 20, wherein the liquid is introduced through a passage entering the interior space into the said heel part.

22. A method according to claim 17, wherein the mould comprises a flexible hollow plastics envelope shaped to correspond generally to the shape of the human foot and shin, and wherein the liquid plastics material is introduced into the plastics envelope to surround the keel part of the endoskeletal structure but substantially without covering the shin part of the structure, whereby, when the introduced plastics material sets, it forms, together with the plastics envelope, a cosmesis comprising (a) a resilient body containing the keel part, which body includes a flexible outer skin and is in the shape of a human foot, and (b) a hollow shell which is integral with the foot body and is in the shape of a human shin.

23. A method according to claim 18, wherein the liquid plastics material is a polyurethane material.

24. A method according to claim 22, wherein the liquid plastics material is a polyurethane material.

25. A method of making a below-knee lower limb prosthesis comprising providing a unitary foot and shin component as claimed in claim 1, the cosmesis comprising, in the region of the shin member, a hollow flexible shell which surrounds the shin member and extends beyond the proximal end of the shin member, providing a proximal limb component including a stump socket of a required size, securing the foot and shin component to the proximal limb component with the proximal portion of the shell rolled down, and unrolling the proximal portion of the shell proximally to fit around at least the distal portion of the socket.

* * * * *